United States Patent [19]

Bartsch

[11] 4,421,923

[45] Dec. 20, 1983

[54] RING SUBSTITUTED CROWN ETHERS AND METHOD OF PRODUCING SAME

[75] Inventor: Richard A. Bartsch, Lubbock, Tex.

[73] Assignee: PCR Research Chemicals, Inc., Gainesville, Fla.

[21] Appl. No.: 215,680

[22] Filed: Dec. 12, 1980

[51] Int. Cl.$^3$ .............................................. C07D 323/00
[52] U.S. Cl. .................... 549/349; 549/348; 548/216; 525/384
[58] Field of Search ................. 260/338; 549/348, 349

[56] References Cited

U.S. PATENT DOCUMENTS

| | | | |
|---|---|---|---|
| 3,427,326 | 2/1969 | Dietrich et al. | 260/338 X |
| 3,686,225 | 8/1972 | Pedersen | 260/340.3 |
| 3,763,188 | 10/1973 | Krespan | 260/338 |
| 3,860,611 | 1/1975 | Krespan | 260/338 |
| 3,966,766 | 6/1976 | Lehn | 260/327 R |
| 3,997,565 | 12/1976 | Kauer | 424/278 X |
| 4,001,279 | 1/1977 | Cram | 260/456 R X |
| 4,024,158 | 5/1977 | Kauer | 424/278 X |
| 4,256,859 | 3/1981 | Woo | 260/338 X |

FOREIGN PATENT DOCUMENTS 1440716 4/1966 France .............................. 260/338

OTHER PUBLICATIONS

Ashby et al., Synthetic Communication, (4), 1974, pp. 113-117.
Izatt et al., J.A.C.S., 99, (1977), 2365-2366.
Tomoi et al., C. A., 90, (1979), 121561a.
C. A. Chem. Substance Index, 90, (1979), p. 4132cs.
C. A., 37; (1943), 3736-4 Khorosch et al.
C. A., Okahara et al., 95, (1980), 7360n.
Gokel et al., "Synthesis", (1976), p. 168.
Fuson, "Advanced Organic Chemistry", (1950), pp. 123-125, John Wiley & Sons.
Streitwieser et al., "Introduction to Organic Chemistry", (1976), pp. 236-237, MacMillan.
Pedersen; J.A.C.S., 89, (1967), pp. 7017-7036.
Pedersen; J.A.C.S., 92, (1970), pp. 391-394.
Tomoi et al., Tetrahedron Letters, 36, (1979), pp. 3485-3486.
"Noller, The Chemistry of Organic Compounds", 3rd ed., (1965), pp. 150-151, W. B. Saunders Co.
Tomoi et al., Tetrahedron Letters, 33, (1978), pp. 3031-3034.

*Primary Examiner*—Joseph Paul Brust
*Attorney, Agent, or Firm*—R. A. Sturges; M. H. Douthitt

[57] ABSTRACT

There is provided a new class of crown ethers characterized by an —OH functional group attached to a carbon atom in the heterocyclic ether ring portion and derivatives thereof. A novel process for making such crown ethers is also provided which is characterized by reacting a bisphenol ether with an epihalohydrin to effect ring closure and provide the appendant —OH group.

These products are especially useful as complexing agents.

6 Claims, 1 Drawing Figure

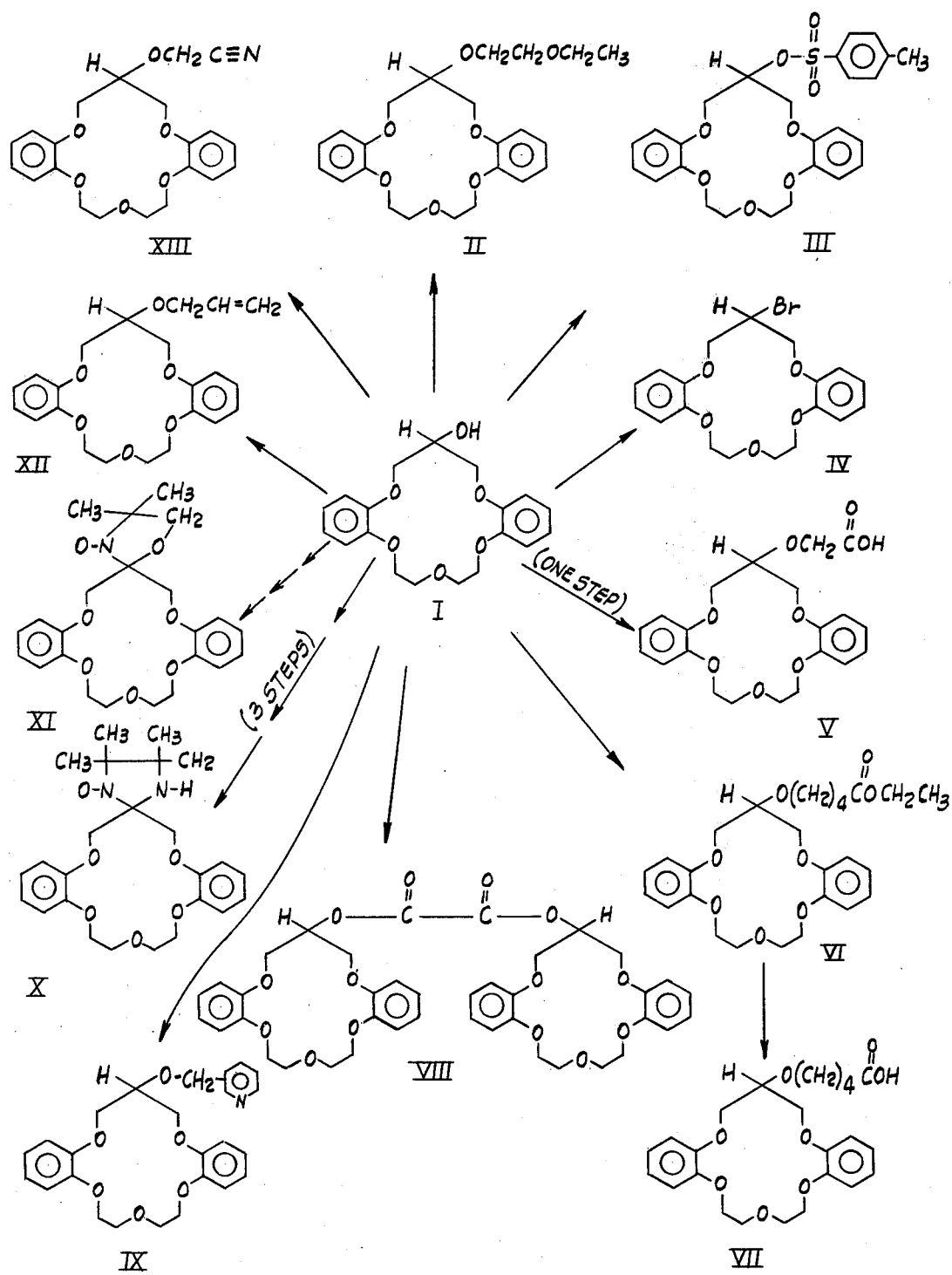

RING SUBSTITUTED CROWN ETHERS AND METHOD OF PRODUCING SAME

This invention relates to certain modified "crown" ethers, and more particularly to crown ethers characterized by functionality appended to the heterocyclic ether ring portion of the molecule, and to a process for producing them.

BACKGROUND OF THE INVENTION AND PRIOR ART

Macrocyclic polyethers or "crown ethers" have been known for a number of years, C. J. Pedersen of DuPont being credited with the invention thereof (See U.S. Pat. No. 3,687,978; and Pedersen, J. Amer. Chem. Soc., 89, 7017–7036 (1967). These materials have particular utility in their remarkable ability to complex with numerous elements (See U.S. Pat. No. 3,686,225 to Pedersen). A typical crown ether has the following structure:

(A)

2,3,11,12-Dibenzo-1,4,7,10,13,16-hexoxacyclooctadeca-2,11-diene
(Dibenzo-18-crown-6)

Since the development of the original crown ethers, considerable work has been done on substituted crown ethers. For example, the patent to Kauer, U.S. Pat. No. 3,997,565, discloses certain acyl crown ether oximes, oxime ethers and oxime esters useful as complexing agents, dispersing agents for carbon black, and antiviral agents. In U.S. Pat. No. 4,024,158 Kauer discloses various aroyl crown ethers having a wide variety of substituent groups directly attached to a benzo group. U.S. Pat. No. 4,001,279 to Cram shows another modification of crown ethers to provide chiral, hinged and functionalized host multiheteromacrocycles containing oxygen, nitrogen and/or sulfur and possessing holes sized to afford selective complexation of specific guest substances, the provision of ortho positioned side chain substituents or "arms" bearing terminal functional groups which act as counterions or additional complexing sites, and the provision of remote position side chain substituents used to control solubility and volatility properties or to bond the multiheteromacrocycles to solid supports.

Another class of crown ethers is described as "cryptates" which are especially useful in forming stable complexes as described in U.S. Pat. No. 3,966,766 to Lehn, and Tetrahedron Lett., 1979, (36), 3485–3486 (Eng.).

The foregoing references are illustrative of some of the modifications of that important new class of materials. Generally speaking, the simpler crown ethers are made by reacting 2 molecules of a dihydric phenol, e.g., catechol, with 2 molecules of an alkyl dihalide or alkyl ether dihalide in the presence of 4 molecules of alkali metal hydroxide, e.g., NaOH (See Pedersen U.S. Pat. No. 3,687,978). The other illustrative references referred to above disclose similar reactions.

The present invention provides a novel method of making a modified crown ether of the various types described in the art having functionality which, instead of being attached directly or indirectly to a hydrocarbyl ring (for example, a benzo group), is attached directly to a carbon atom in the polyether portion of the molecule. All the products hereof may be used as complexing agents in the same way and for the same purposes as chelating agents.

The process for making these novel crown ethers which have a functional group "handle" on the polyether ring is also believed to be novel. It has been found not to be practical to introduce functional groups onto the polyether rings of existing crown ethers. Therefore, such functional groups must be incorporated prior to or concomitant with ring closure. A reported example of the synthesis of crown ethers bearing functional group "handles" on the polyether rings (a), (b), and (c), is shown below. While it is possible to prepare the "functionalized"

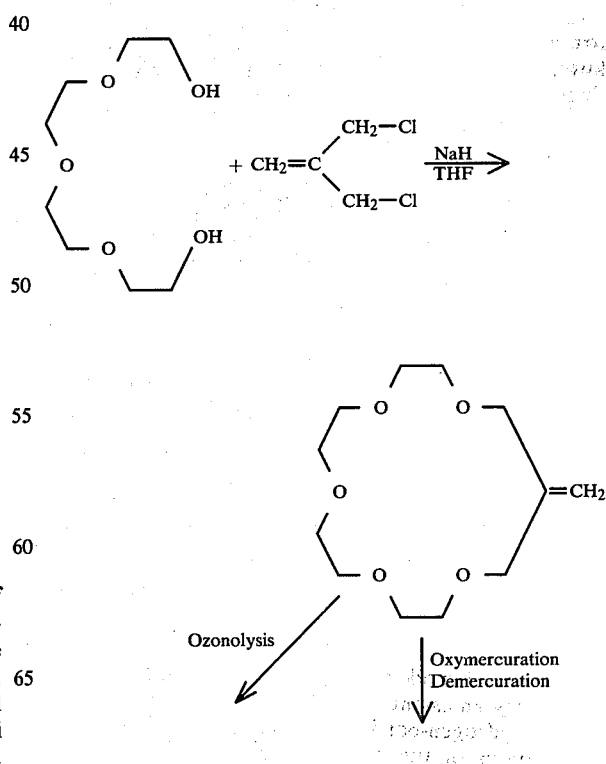

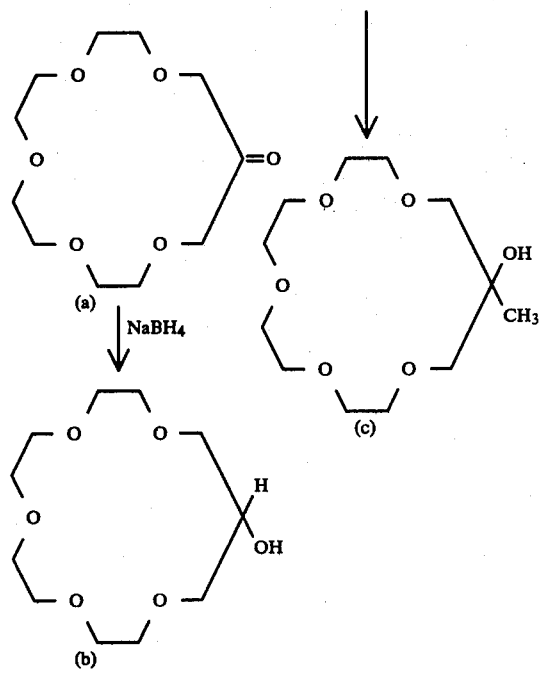

crown ethers (a), (b), and (c) by these reaction series, the process, albeit novel, is costly and does not lend itself to industrial application.

What has now been found is an industrially practical synthesis for functionalized crown ethers wherein the polyether ring is provided with at least one functional group.

The closest prior art of which I am aware is an article entitled "A Modified Synthesis of Dibenzo-18-Crown-6-Polyether and Related Macrocycles", by Ashby et al., "Synthetic Communications", 4(2), 113–117 (1974). According to this article an amidic diphenol (d) was reacted with sodium hydroxide and 1-chloro-2,3-epoxypropane under conditions of high dilution to produce a low yield (12%) of cyclized product (e). Examination of three

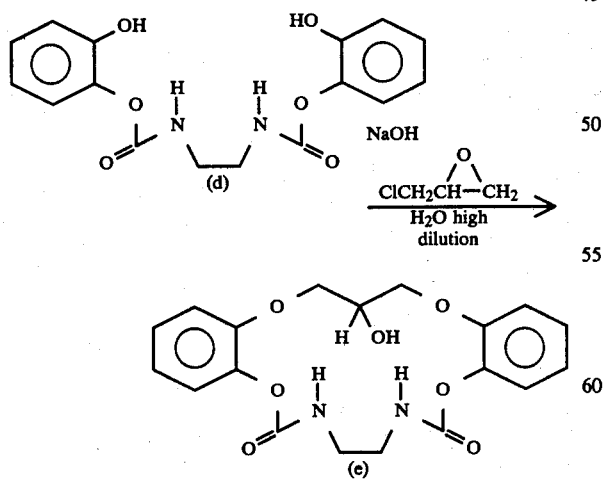

dimensional models suggests that the amide linkages may play an essential role in the ring closure reaction. First, hydrogen-bonding interactions may produce conformations of the diphenoxide (f) in which the two negatively charged oxygens are brought into proximity, thus favoring ring closure. Alternatively, one of the

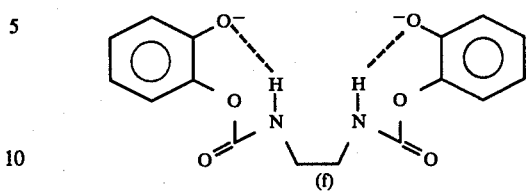

amide groups may facilitate ring closure by producing favorable interactions within a reaction intermediate, for example (g). Therefore, it seems

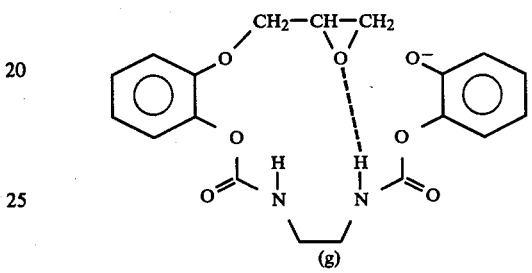

reasonable to expect that the amide groups were important to the success of the ring closure reactions (d)→(e).

In the case of the present invention, the ring heteroatoms are oxygen and no amide linkages are present. Surprisingly, it has been found that effective ring closure occurs with the diphenol ethers used in the present invention and that the yields of ring closure products are several times higher than that reported by Ashby et al., for the cyclization of the amidic diphenol (d).

According to the prior art the yield was 12%. A three dimensional model of the starting material prior to ring closure indicates that the presence of N tends to favor ring closure. In the case of the present invention where the hetero atoms are oxygen, ring closure is not favored. Surprisingly, however, not only has effective ring closure been found to occur with the diphenol ethers used in the present invention, but the yield is several times that obtained where nitrogen is present in the ring.

BRIEF STATEMENT OF THE INVENTION

Briefly stated, the present invention is in a new class of crown ethers characterized by a functional group directly attached to a carbon atom in the oxyheterocyclic ring. The compounds have a general formula as follows:

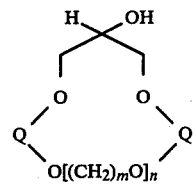

wherein Q is a bivalent organic cyclic radical, vicinal carbon atoms of which are directly attached to heterooxygen atoms in an oxo heterocyclic ring; and m and n are integers independently selected from 1, 2 and 3.

These products are produced by a process which is characterized by the step of reacting in an aqueous medium a dihydroxy ether having the general formula:

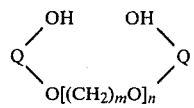

wherein Q, m and n have the meanings described above, with an epihalohydrin in the presence of an alkali metal hydroxide.

BRIEF DESCRIPTION OF THE DRAWINGS

Reference may be had to the annexed drawing which illustrates utilities of a preferred embodiment (I) of this invention in making useful derivatives, II to XIII.

DETAILED DESCRIPTION OF THE INVENTION AND SPECIFIC EXAMPLES

The dihydroxy ether starting materials of the present invention are conveniently produced by reacting an ortho dihydroxy cyclic compound such as catechol, with a dihalide in the presence of an alkali metal hydroxide, e.g., NaOH. The cyclic group may be aromatic such as phenylene, naphthylene, or phenyl phenylene. The ring of the dihydroxy cyclic compound may carry one or more substituent hydrocarbyl groups, e.g., methyl, ethyl, vinyl, propyl, isopropyl, butyl, t-butyl, amyl, isoamyl, hexyl, cyclohexyl, octyl, 2-ethylhexyl, lauryl, etc., halogen such as chlorine, bromine, fluorine; alkoxy, e.g., methoxy, ethoxy, t-butoxy, hexoxy; keto, e.g., acetyl, acetonyl; nitro, and the like, such substituents being virtually inactive and unaltered under the reaction conditions.

To illustrate the ether forming reaction, catechol, bis-2-chloroethyl ether and NaOH are used in a reaction according to the following:

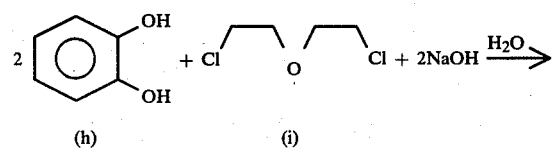

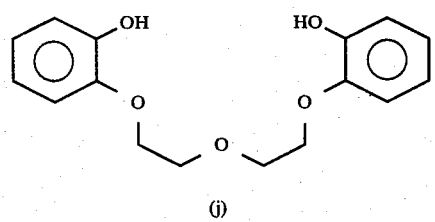

The ether (j) is then reacted with an epihalohydrin and sodium hydroxide in water to give the crown ether (d):

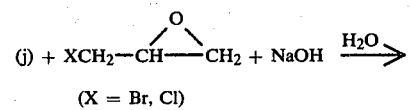

(X = Br, Cl)

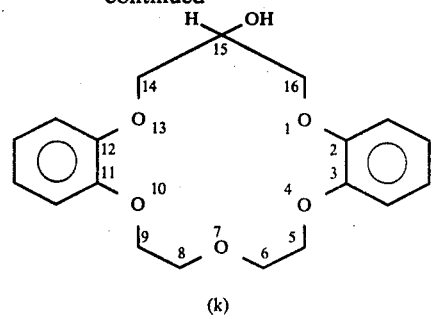

Compound (k), identified as I in the annexed drawing, is a preferred new compound, and is the best mode known to me illustrative of the invention in this type of compound.

In this two step synthesis, the first step is the reaction of bis-2-chloroethyl ether with catechol and sodium hydroxide in water. An excess of catechol and a controlled amount of base are used to produce the diphenol (j) without employing a blocking group. The diphenol (j) precipitates from the reaction solution and is washed with water to remove contaminating catechol. The diphenol (j) is then recrystallized from methanol. Based upon the limiting reagent bis-2-chloroethyl ether (i) 40% yields (200 gs) of diphenol (j) have been obtained.

The second or ring closure step involves the reaction of the diphenol (j), sodium hydroxide, and an epihalohydrin in water to form the crown ether (k) with the OH "handle" attached directly to a carbon atom on the polyether ring. As the ring closure proceeds, the hydroxy substituted crown ether (k) precipitates from the reaction solution and is removed by filtration. The crude dibenzo hydroxy crown ether (k) may be purified by recrystallization from water. At a scale giving 50 grams of (k), the yield has been found to be 70% of crude dibenzo hydroxy crown ether (k).

A similar compound containing 6 polyether oxygen atoms can be made following a similar procedure. The higher oxygen content diphenol is more difficult to make than the 5-oxygen product. The ring closure step proceeds easily in all cases.

It is important to note that the ring closure reaction does not occur when 1,3-dichloro-2-propanol is used in place of epihalohydrin. Epichlorohydrin and epibromohydrin work equally well.

Chemical oxidation of the dibenzo hydroxy crown ether (k) with Na$_2$Cr$_2$O$_7$ and H$_2$SO$_4$ in acetone yields dibenzo keto crown ether (l), a novel compound having the following general formula:

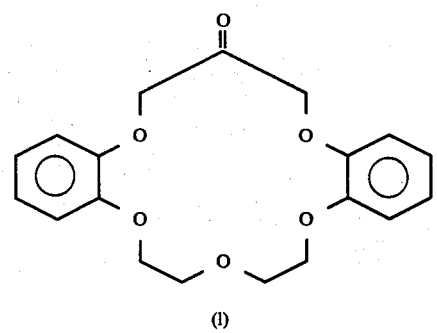

Hydrogenation of the dibenzo hydroxy crown ether (k) under pressure with Ruthenium on carbon contact catalyst yields dicyclohexyl hydroxy crown ether (m) a novel compound having the following general formula:

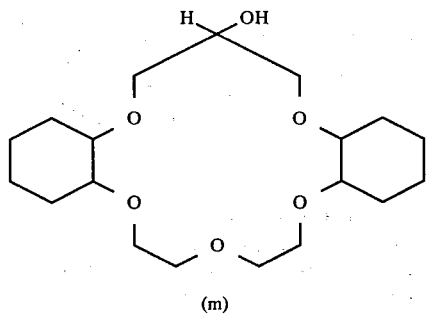

(m)

Attachment of various "arms" to the functional group "handle" of dibenzo hydroxy crown ether (k) enables production of interesting novel compounds such as novel dibenzo carboxylic acid crown ether (n, with R=H), its esters, salts, amides, etc. The carboxylic acid derivative is particularly interesting because in basic media the carboxylic acid proton is removed to provide a crown ether bearing an anionic group, (n, with R=—). The novel oxyacetic acid derivative (n, with R=H) has the following general formula:

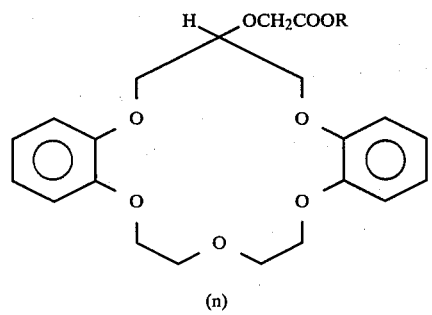

(n)

To produce the oxyacetic acid derivative (numeral V in the annexed drawing), the dibenzo hydroxy crown ether (k) is converted to the sodium alkoxide. This is then reacted with methyl bromoacetate forming a novel ester (n, with R=methyl) which is subsequently acid hydrolyzed to the dibenzo oxyacetic acid crown ether (n, with R=H).

Metal complexes of the various derivative products described herein may be prepared by dissolving the crown ether in a suitable organic solvent, e.g., acetone, adding a salt containing the metal cation to be complexed and heating the mixture to boiling until all of the solid material is dissolved. The mass is then evaporated to dryness and extracted with a second suitable organic solvent, e.g., chloroform. This extract may also be evaporated to dryness and the residue recrystallized from an appropriate solvent or combination of solvents. The recovered complex can be used for conducting reactions in organic media.

It becomes convenient at this point to provide specific illustrative examples of preparations in accordance with this invention. It will be understood that these examples are for illustrative purposes only and are not to be deemed as limiting the scope of the invention.

EXAMPLE I

Synthesis of 1-Hydroxy-(4,5)(13,14)-dibenzo-3,6,9,12,15-pentaoxacyclohexadecane

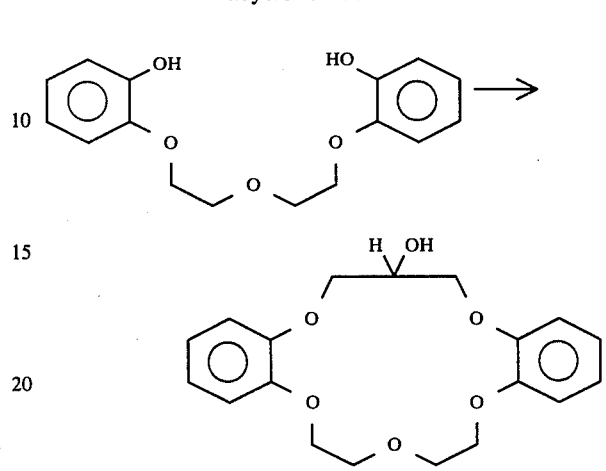

A mixture of 52.0 grams of bis(2-[2-hydroxyphenoxy)ethyl) ether, E. P. Kyba et al., J. Am. Chem. Soc., 99, 2564 (1977), 3.5 liters of water, and 130 milliliters of 3 N aqueous NaOH was heated under nitrogen at 90° C. until a homogeneous solution was obtained. The solution was cooled to 50° C., and 15.8 milliliters of epichlorohydrin was added to the stirred solution over a period of 2 hours at 50° C. After the addition was completed, the reaction mixture was stirred at 50° C., for 2 hours. The mixture was then cooled to 10° C. and the solid product was filtered and air-dried, yielding 40.9 grams (69.3%) of crude 1-hydroxy-(4,5)(13,14)-dibenzo-3,6,9,12,15-pentaoxacyclohexadecane. Recrystallization from hexane produced 35.0 g (58.3%) of white crystals with a melting point 112°–114° C. An analytical sample was recrystallized from water to give white needles with a melting point of 122°–123° C. In general, the yields ranged from about 58% to 70%.

Elemental Analysis: Theoretical: %C=65.90, %H=6.36. Found: %C=65.76, %H=6.20.

Spectra: PMR (in $CDCl_3$, ppm): delta 6.96 (m, 8H), delta 4.28 (m, 4H), delta 4.22 (m, 4H), delta 3.87 (m, 4H), delta 4.45 (m, 1H), delta 3.41 (broad s, 1H).

IR (KBr): 3400 cm$^{-1}$ (broad) (OH). 1105 and 1020 cm$^{-1}$ (C—O—C).

This example represents the best mode known to me for producing a novel crown ether with a "handle".

EXAMPLE II

Synthesis of 1-Hydroxy-(4,5)(16,17)-dibenzo-3,6,9,12,15,18-hexaoxacyclononadecane

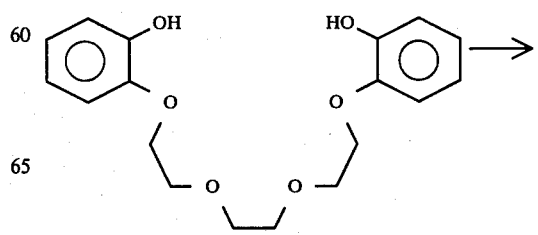

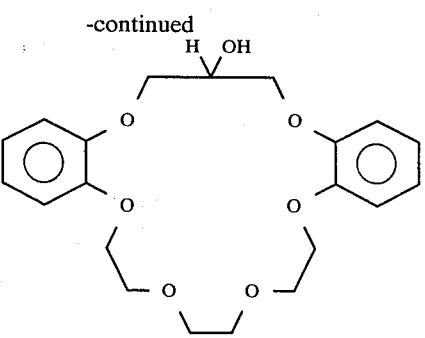

Under a nitrogen atmosphere, 5.0 grams (0.015 mole) of 1,8-bis-(2-hydroxyphenoxy)-3,6-dioxaoctane hydrate and 1.7 grams (0.030 mole) of potassium hydroxide in 350 milliliters of water was heated to 50° C. Epichlorohydrin (1.3 milliliter, 0.017 mole) was added dropwise over a period of 1 hour. The reaction solution was stirred at 50° C. for 5 hours. The reaction mixture was cooled in an ice bath. The aqueous solution was decanted away from the solidified oil. The solid was washed with 200 milliliters of water. The solid was dissolved in dichloromethane and, after drying with magnesium sulfate, the dichloromethane was evaporated in vacuo. The white crystalline residue weighed 3.0 grams (51%) and had a melting point of 72°–73° C. For elemental analysis, a sample of this material was chromatographed on silica gel with diethyl ether as eluent to give white crystals with a melting point of 74° C.

Elemental Analysis: Theoretical: %C=64.60, %H=6.66. Found: %C=64.68, %H=6.55.

Spectra: PMR (in CDCl$_3$, ppm): delta 6.88 (m, 8H), delta 4.43 (broad singlet, 1H), delta 3.30 (m, 1H), delta 4.13 (m, 4H), delta 3.37 (m, 8H), delta 4.07 (m, 4H).

IR (neat): 3480 cm$^{-1}$ (broad, OH). 1120 and 1045 cm$^{-1}$ (C—O—C).

Mass Spec: Parent ion at 390.

EXAMPLE III

Synthesis of 1-Hydroxy-(4,5)(13,14)-dicyclohexano-3,6,9,12,15-pentaoxacyclohexadecane

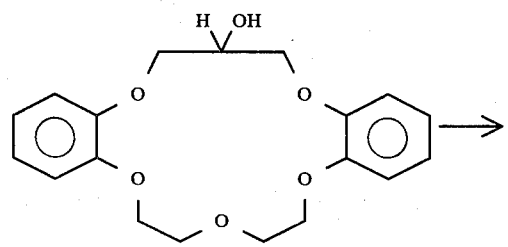

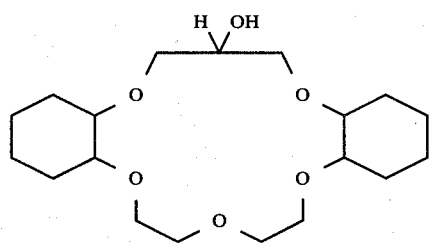

1-Hydroxy-(4,5)(13,14)-dibenzo-3,6,9,12,15-pentaoxacyclohexadecane (4.85 grams) was dissolved in 100 ml of absolute ethanol and was hydrogenated (about 1200 psi, 100° C., 15 hours) over 0.50 g of 5% Ru on carbon catalyst. The catalyst was removed by filtration and was rinsed with an ethanolacetone mixture. The rinsings were added to the reaction product solution followed by removal of the solvents in vacuo. The residue was chromatographed on silica gel with diethyl ether as eluent giving, in addition to recovered starting material, 1.50 g (30%) of white solid with a melting point range of 90°–95° C. Thin layer chromatography on silica gel plates with diethyl ether as the developing solvent showed two spots as would be expected for two geometrical isomers of 1-hydroxy-(4,5)(13,14)-dicyclohexano-3,6,9,12,15-pentaoxacyclohexadecane.

Elemental Analysis: Theoretical: %C=63.70, %H=9.50. Found: %C=63.57, %H=9.66.

Spectra: PMR (in CDCl$_3$, ppm): delta 1.55 (m, 16H), delta 3.67 (m, 16H), delta 3.98 (m, 1H), delta 3.12 (broad s, 1H).

IR (KBr pellet): 3440 cm$^{-1}$ (broad, OH), 1083 cm$^{-1}$ (C—O—C).

EXAMPLE IV

Synthesis of 1-(OCH$_2$CO$_2$Me)-(4,5)(13,14)-dibenzo-3,6,9,12,15-pentaoxacyclohexadecane

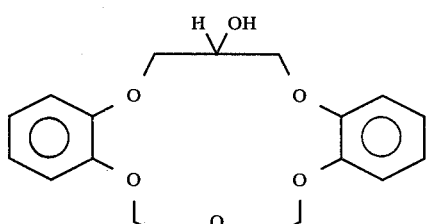

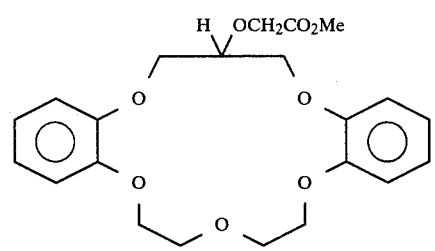

Under nitrogen, 0.30 grams (6.0 millimole) of 50% oil protected sodium hydride was washed with pentane. To the washed sodium hydride were added 200 milliliters of dry tetrahydrofuran and 2.0 grams (5.8 millimoles) of 1-hydroxy-(4,5)(13,14)-dibenzo-3,6,9,12,15-pentaoxacyclohexane. When evolution of hydrogen ceased, 1.0 gram (6.5 millimole) of methyl bromoacetate in 25 milliliters of tetrahydrofuran was added. After refluxing under nitrogen for 24 hours, the reaction mixture was cooled, filtered, and the solvent was removed in vacuo producing 1.72 grams (69%) of the title compound. Recrystallization from 2-methoxyethanol gave white needles with a melting point of 155°–156° C.

Elemental Analysis: Theoretical: %C=63.16, %H=6.22. Found: %C=63.01, %H=6.36.

Spectra: PMR (in CDCl$_3$, ppm): delta 6.83 (m, 8H), delta 4.53 (s, 2H), delta 3.72 (s, 3H), delta 4.27 (m, 5H), delta 4.08 (m, 4H), delta 3.85 (m, 4H).

IR (neat): 1755 cm$^{-1}$ (C=O).

EXAMPLE V

Synthesis of
1-(OCH₂CO₂H)-(4,5)(13,14)-dibenzo-3,6,9,12,15-pentaoxacyclohexadecane

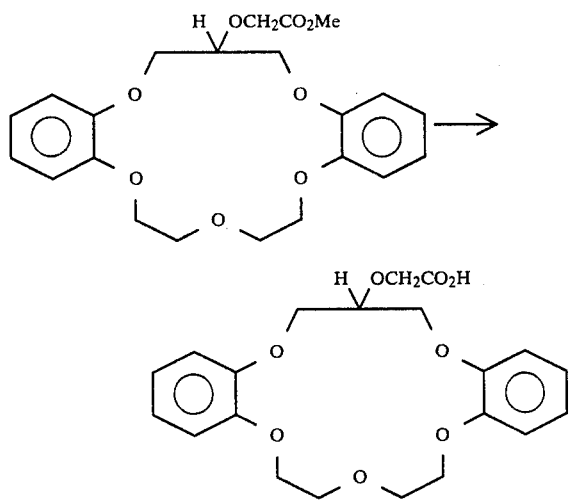

To a solution of 1.2 grams (2.8 millimoles) of 1-(OCH₂CO₂Me)-(4,5)(13,14)-dibenzo-3,6,9,12,15-pentaoxacyclohexadecane in 120 milliliters of methanol was added 1.0 gram (27 millimoles) of sodium hydroxide in 1 milliliter of water. The solution was refluxed for 6 hours. After concentrating to a volume of 5 milliliters, the solution was diluted with water to 50 milliliters. The suspension was extracted twice with dichloromethane. When the aqueous layer was acidified with concentrated hydrochloric acid to a pH of 1, white crystals (0.9 grams, 77%) separated. When recrystallized from EtOH-H₂O, white needles were obtained with a melting point of 166°-166.5° C.

Elemental Analysis: Theoretical: %C=62.38, %H=5.94. Found: %C=62.43, %H=6.16.

Spectra: PMR (in DMSO-d₆, ppm): delta 6.89 (m, 8H), delta 4.33 (s, 2H), delta 4.15 (m, 4H), delta 3.85 (m, 4H), delta 4.06 (m, 4H), delta 4.56 (m, 1H).

IR: 3600-2260 cm⁻¹ (OH), 1765 cm⁻¹ (C=O).

The novel compounds of the present invention are useful as highly efficient and selective metal ion complexation agents. These compounds can also be used to synthesize the compounds II to XIII in the annexed drawing by procedures such as have been illustrated above. The acid compounds, e.g., Example V, above, may be used to remove metal ions from waste waters according to the following scheme:

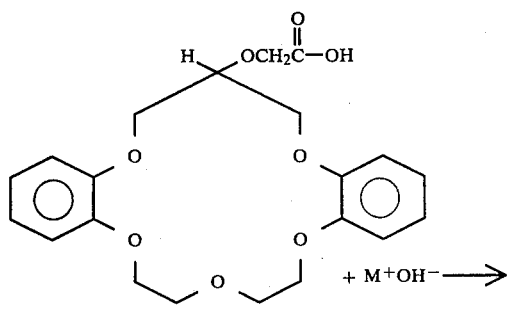

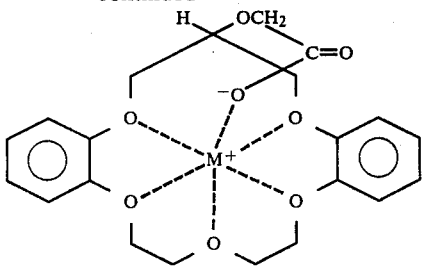

where the identity of the counteranions in metal crown ether complexes strongly influences the capability of crown ethers to extract selected metal ions and carry them into solution in an organic solvent phase for recovery. The acid compound shown as Example V has also been used to separate lithium isotopes by partitioning lithium ions between an aqueous and an organic phase.

The hydroxyl functional group also provides a site for attaching the crown ethers to polymers, for example:

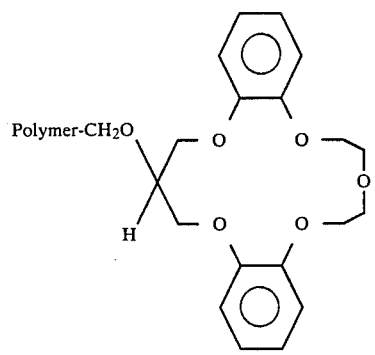

Such materials are useful in selective metal ion extraction and in polymers for chromatography.

Compounds such as VIII in the annexed drawing are useful in complexing large cations such as uranium.

The compound (1) above is useful in forming spin-labled crown ethers according to the following reaction sequence:

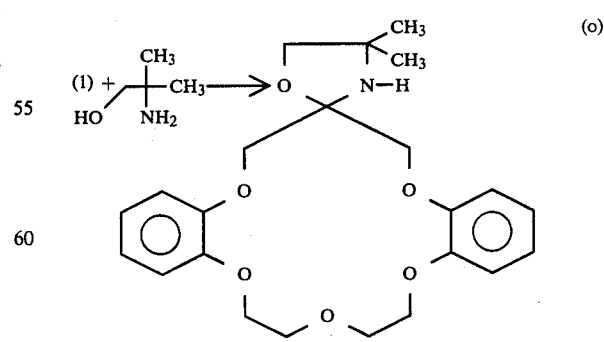

Compound (o) is stable and can be isolated. When chemically oxidized, it yields the novel stable free radical compound (p) (XI in the annexed drawing).

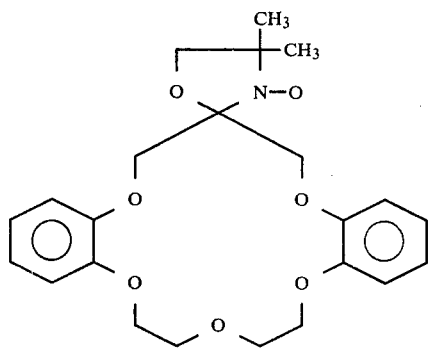

What is claimed is:

1. A process for making a macrocyclic polyether which comprises reacting in an aqueous medium a dihydroxy ether having the general formula:

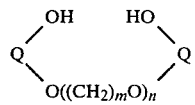

wherein Q is a bivalent organic cyclic radical containing at least 6 carbon atoms and selected from phenylene, naphthylene, phenyl phenylene and mono or poly-substituted phenylene, naphthylene, and phenyl phenylene where the substituent group is selected from hydrocarbyl groups containing from 1 to 12 carbon atoms, halogen, alkoxy groups containing from 1-6 carbon atoms, acetyl, acetonyl, and nitro, vicinal carbon atoms of which are directly attached to oxygen atoms in the dihydroxy ether; and m and n are integers selected from 1, 2 and 3, with an epihalohydrin in the presence of an alkali metal hydroxide and recovering a product having the general formula:

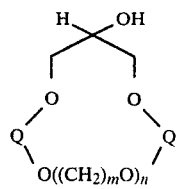

wherein Q, m, and n have the meanings ascribed above.

2. A process for making a macrocyclic polyether which comprises reacting a temperature of 50° C. under nitrogen in an aqueous medium a dihydroxy ether having the general formula:

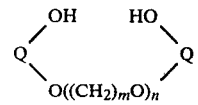

wherein Q is selected from phenylene, naphthylene, phenyl phenylene and cyclohexylene, and mono- or poly-substituted phenylene, naphthylene, and phenyl phenylene, where the substituent group is selected from hydrocarbyl groups containing from 1 to 12 carbon atoms, halogen, alkoxy groups containing from 1 to 6 carbon atoms, acetyl, acetonyl, and nitro, vicinal carbon atoms of which are directly attached to oxygen atoms in the bis-(hydroxy) ether and m and n are integers selected from 1, 2, and 3 with an epihalohydrin in a mole ratio of about 1:1, in the presence of an alkali metal hydroxide and recovering a product having the general formula:

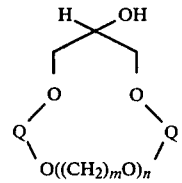

wherein Q, m and n have the meanings ascribed above.

3. A process as defined in claim 1 wherein Q is phenylene.

4. A process as defined in claim 1 wherein Q is naphthylene.

5. A process as defined in claim 1 wherein Q is phenylene and m is 2.

6. The process of claim 1 further characterized by the step of hydrogenating the product, formula B, to form the cyclohexyl derivative.

* * * * *